United States Patent [19]

Bertagnoli

[11] Patent Number: 5,571,109
[45] Date of Patent: Nov. 5, 1996

[54] SYSTEM FOR THE IMMOBILIZATION OF VERTEBRAE

[75] Inventor: Rudolf Bertagnoli, Göttingen, Germany

[73] Assignee: MAN Ceramics GmbH, Deggendorf, Germany

[21] Appl. No.: 297,445

[22] Filed: Aug. 26, 1994

[30] Foreign Application Priority Data

Aug. 26, 1993 [DE] Germany .......................... 43 28 690.9

[51] Int. Cl.$^6$ .......................... A61B 17/70; A61B 17/88; A61B 17/90
[52] U.S. Cl. .......................... 606/61; 606/90; 606/99
[58] Field of Search .......................... 606/60, 61, 90, 606/99, 105, 86; 623/17

[56] References Cited

U.S. PATENT DOCUMENTS

| | | | |
|---|---|---|---|
| 3,486,505 | 12/1969 | Morrison | 606/90 |
| 3,875,595 | 4/1975 | Froning . | |
| 4,545,374 | 10/1985 | Jacobson | 606/90 |
| 4,969,888 | 11/1990 | Scholten et al. . | |
| 5,015,247 | 5/1991 | Michelson . | |
| 5,122,130 | 6/1992 | Keller | 606/61 |
| 5,192,327 | 3/1993 | Brontigan | 606/60 |
| 5,258,031 | 11/1993 | Salib et al. | 623/17 |
| 5,395,372 | 3/1995 | Holt et al. | 606/61 |
| 5,431,658 | 7/1995 | Moskovich | 606/99 |

FOREIGN PATENT DOCUMENTS

| | | |
|---|---|---|
| 0179695 | 4/1986 | European Pat. Off. . |
| 3310833 | 10/1983 | Germany . |
| 3310835 | 10/1983 | Germany . |
| 3505567 | 6/1986 | Germany . |
| 3618193 | 12/1987 | Germany . |
| 3922044 | 2/1991 | Germany . |
| 2017502 | 10/1979 | United Kingdom . |

*Primary Examiner*—Michael Powell Buiz
*Assistant Examiner*—Scott B. Markow
*Attorney, Agent, or Firm*—Robert W. Becker & Associates

[57] ABSTRACT

For a rapid and accurate performance of surgery for the immobilization of vertebrae an implantation system is suggested in the case of which the surgical implements such as drills, chisels, bone milling or routing implements, implant guide implements, cooperate with an ancillary device, which renders possible an exact and speedy mounting of the respectively desired implement. The ancillary device may be an elongated guide instrument which comprises guide rails or a guide cylinder and a spreading device. A spacer, which is inserted into a gap between vertebrae after the same have been urged apart, may also be designed in the form of an auxiliary device.

24 Claims, 13 Drawing Sheets

SYSTEM FOR THE IMMOBILIZATION OF VERTEBRAE

BACKGROUND OF THE INVENTION

The invention relates to an implantation system for the immobilization of vertebrae.

The German patent publication 3,505,567 C discloses a system of this type comprising the use of an implant and an instrument for the introduction of the implant. The implant comprises a solid cylinder with an external screw thread, which is able to be gripped by means of jaws of an implanting instrument at one end. The jaws, which are able to be slid axially in the instrument, have a sharp edged bar on the internal side, may be caused to bite into the implant in order to prevent twisting of the same. Using this known instrument the implant is screwed into a prepared cavity between two adjacent vertebrae, something involving an intricate manipulation.

The European patent publication 179 695 shows an implant which while being designed in the form of a simple disk, possesses lugs in order to secure it in place and using which the implant is screwed onto the bone of the vertebra. The screwing operation does however involve a slow manipulative process.

SHORT SUMMARY OF THE INVENTION

One object of the invention is to provide an implantation system for the immobilization of vertebrae which renders possible both a brief duration of the implantation process and also a reliable immobilization of the vertebrae on which surgery is performed.

In order to achieve these and/or other objects appearing from the present specification, claims and drawings, the present invention provides an auxiliary device which renders possible a connection between vertebrae or, respectively, an intermediate space between the same and the implement to be operated by the surgeon. The ancillary device ensures an accurate local association between implements and vertebrae so that the surgeon is spared the time-consuming task of visually positioning and locating devices each time implements are placed in position. The implement is instead positioned, and if necessary also guided, by the auxiliary device, which for the duration of the implanting process is connected with the vertebrae or remains in unmovable contact. The manipulations, such as cutting away bone, excavation of a cavity, and the mounting of the implant are consequently able to be performed in rapid succession and with accurate positioning.

The auxiliary device is in accordance with a first embodiment of the invention in the form of an elongated guide instrument, which is moved as far as the vertebra and defines a certain position in relation to the vertebrae, which is transmitted to the different surgical implements and the implant which is to be mounted.

Elongated instruments able to be moved as far as the site of surgery have been suggested in a large number of different designs (see for example the said German patent publication 3,505,567 C and the U.S. Pat. No. 5,015,247), in which respect it is always a question of a separate surgical implement such as a drill, a chisel, stapling means and the like, whereas on the contrary in the case of the invention it is a question of a universal guide instrument, which is placed in between suitably designed implements such as those noted above and for implants to be inserted. The result is the possibility of rapidly performing and accurately fitting of the implant for immobilization of vertebrae. The guide instrument essentially comprises an elongated hollow body with a closed or open cross section, which is constituted either by a tubular structure or by one or more mutually parallel rails, which are connected together rigidly at one end at least.

Guide instrument have been proposed in the U.S. Pat. Nos. 3,875,595 and 4,969,888. Known instruments comprised a tube with a sufficient internal diameter to allow the passage of the operating tools as far as the vertebrae. After the production of a cavity for the implant a bladder-like implant is introduced through the guide instrument into the cavity and charged with a liquid. Such an implant adapts itself automatically to the wall of the prepared cavity. Accurate fitting of preformed, stiff implants is on the contrary not possible with such known instrument.

The guide instrument in accordance with the invention then on the contrary possesses the advantage that it is suitable both for guiding various different operating tools as also for the introduction test implants as well as being suitable for the introduction of the implant as such. The operating tools, as for instance the extraction by suction of a vertebral disk or of bone parings, drills, drilling templates, chisels and the like are also provided with guide means, which cooperate with the guide means of the guide instrument. Thus it is possible to accurately prepare the cavity for the implant, test the same using a sample or dummy implant and accurately fit the implant in the column in rapid succession. The guide instrument ensures accurate positioning of the various different operating instruments and of the implant.

The guide instrument may, as described in the said U.S. Pat. No. 4,969,888, bear pins on the end adjacent to the vertebra, which for anchoring the guide instrument penetrate the bone substance of the vertebra.

An other advantageous feature of the invention is such that the guide instrument is provided on its end which is to be introduced between the vertebrae with a spreading device so that the instrument simultaneously serves as a spreading instrument for the two vertebrae. The spreading operation may for example be performed by means of spreading wedges. The spreading device simultaneously performs the function of a spacer during anchoring the vertebrae in the spread-apart position.

The auxiliary device in the form of a guide instrument in accordance with the invention consequently constitutes a universal instrument, which renders possible rapid and accurate work in the course of surgery.

The auxiliary device may, according to a further embodiment of the invention, be in the form of a spacer, which possesses at least two distance members inserted into the intermediate space between two vertebrae after a spreading operation so that they maintain the increased distance apart for the duration of implanting surgery. The spacer hence defines an accurate position in relation to the vertebrae so that it simultaneously functions as a guide or for positioning surgical implements and furthermore implants.

In order to have a design fully consonant with the function of positioning and guiding, the distance members are rigidly connected together by means of a connecting element in the form of a link so that the relative position thereof is permanently set.

The link-like connecting element is preferably arranged to be perpendicular to the distance members in such a manner that after introduction of the distance members the connecting element abuts the surface of the vertebra around the site of surgery. The connecting element may be an open or split ring, half a ring or a U-like or V-like structure, whose internal diameter is so large that the site of surgery will remain completely accessible.

The distance members may be solid or hollow cubes, which extend as far as the rear edge of the vertebrae. In the case of distances between the vertebrae of fair size it is possible to utilize suitably shaped distance members of band material.

The distance members will, in accordance with the specific design thereof enter into the widened gap in a fashion which is either parallel or oblique in relation to the longitudinal axis of the spreading forceps and as far as possible toward the edge of the vertebra in order to not to interfere with surgery. Thereafter the spreading forceps is retracted so that access to the site of surgery is completely free.

The distance member in accordance with the invention offers the advantage of allowing rapid preparation for surgery as such and in no way interfering with handling of equipment or with the access to the site of surgery. So far the gap between the vertebrae has been maintained in the widened condition with struts applied externally to the adjacent vertebrae, such struts increasing the size of the site for surgery and possibly restricting free access of the instrument in space, apart from the fact that drilling operations, making screw joints and similar processes mean that the application of such spacers is extremely slow.

The connecting element and any distance members as well may, in accordance with a further embodiment of the invention, be so designed that they perform or are able to assume a guiding function or exact positioning for the surgical implements, which in the course of surgery are employed by the surgeon at the site of surgery. This may be due to the fact that the surgical implements possess guide spurs, which are guided by the opposite sides of the distance members.

In accordance with a preferred embodiment of the invention the connecting element is provided with knobs or pins, which cooperate with suitable recesses or drilled holes on and in the surgical implements. This means that the surgical implement is slipped onto the connecting element, utilized and then taken off again. This manipulation will only require processing time but not however additional time which would have to be employed for the positioning by eye or for measurement. In a similar fashion a holder, which is able to be slipped onto the pins on the distance member, may be employed for the implant, with which the implant is thrust or rammed into the prepared cavity with an accurate fit.

The auxiliary device in the form of a distance member is produced with various different intravertebral gap heights and will be open at one end so that the holder may encircle a spreading forceps for widening the gap between vertebrae.

The auxiliary device designed in the form of a spacer offers the advantage that it is able to be rapidly introduced and is held stably in position by the thrusting force of the vertebrae and because of this remains fixedly in place for the rapid and accurate application of surgical implements and furthermore for the introduction of the implant. By means of a spreading forceps, which simultaneously serves to measure height of the gap between vertebrae, the height of the gap is measured from a scale and a spacer with suitably high distance members is selected and inserted directly into the intermediate space, by holding the connecting element, the distance member being in this case held on the connecting element. Owing to the arcuate design of the connecting element there will be no collision with the spreading implement. Thereafter the spreading implement is withdrawn and surgery commenced, which will merely comprise applying one surgical implement after the other and utilizing the same and then removing them again.

In keeping with yet another possible form of the invention an implant is provided which may be guided in an implement and which besides having the necessary anatomical and mechanical properties, comprises guide means, which render possible rapid and exact placement of the implant. Using an elongated guide implement it is possible to introduce the implement through the tissue as far as the site of implantation while only requiring a small cross sectional area. This means that it is possible using the implant able to be guided in accordance with the invention furthermore, to perform implantation without large operation scars being left on the patient. This opens up the possibility of performing surgery for vertebral immobilization as ambulant treatment.

A still further advantage is that sample implants with the same configuration manufactured of metal may be employed in order to for instance to check positioning intraoperatively with diagnostic equipment, if the final implant consists of synthetic resin for instance and is free of x-ray contrast agent.

The implant is an integral, solid or partly hollow component, which in principle may possess any anatomically expedient configuration. The configuration will depend on the anatomical features, on the convenience of an insertion instrument and/or in accordance with features inherent in the manufacture of the implant. The implant will preferably comprise fiber reinforced material and more particularly carbon fiber reinforced synthetic resin.

As a general point, the implant is intended to permanently join the vertebrae together; it is however also suitable for providing a temporary supporting function and the invention furthermore contemplates the provision of resorbable implants.

In accordance with a further development of the invention which is readily produced the implant is in the form of a solid or hollow rectangular block or cylinder, which in the longitudinal direction possesses at least one guide groove and/or guide key.

The U.S. Pat. No. 4,834,757 discloses rectangular blockklike, hollow or solid means for the immobilization of vertebrae, which however only possess holes in order to receive an instrument with which the implant is inserted without any guiding action, there being then danger of skew positioning of the implant.

In accordance with a preferred embodiment the implant has, starting at one terminal surface, openings for staples in order to prevent slipping of the implant out of position.

It is more especially in the case of cervical vertebrae that arcuate or U-like implants are suitable, whose free limbs or, respectively, lateral portion possess the guide means. Such an implant can be inserted horizontally or on end, that is to say with each limb or side portion in contact with a vertebra. In accordance with a further development of the invention such U-like implants are made elastic so that they can be inserted with a biasing or prestressing action in order to hold themselves in position.

U-shaped implants or other implants provided with an opening through them are preferably filled with bone substance in the free space. Since such manipulation is performed intraoperatively, it must be capable of being implemented rapidly. Accordingly such implants are, in accordance with the invention, used in association with bone presses, whose configuration is adapted to that of the opening. Taking into account the height of the implant the bone press will be so designed that after the introduction of the bone material it merely has to be put in place by the surgeon and thrust until abutment takes place. The method of filling with such bone presses is rapidly performed and leads to a secure fixation of the bone material in the implant.

For securing in position and promoting growth onto the implant at the surfaces cooperating with the vertebrae the same are grained, roughened and/or provided with openings through which the bone substance may come into contact with the adjacent vertebrae.

The invention furthermore contemplates an implantation system for vertebral immobilization comprising several components collected together as a set and adapted to cooperate with each other, which comprise at least one guide instrument and/or at least one spacer, at least one surgical implement adapted to cooperate with the spacer and/or the guide instrument, and an implant.

The implantation system will as a rule include a guide instrument and at least one surgical implement set comprising a suction, drilling and/or surgical chisel, a hook for the insertion and withdrawal of a test implant, a drill template, a ramming implement for thrusting the implant home in a slightly undersize bone recess and furthermore, if necessary, staples and a staple holding means (staple holding devices being for instance described in the German patent publication 3,310,835). If several component sets are provided then each will be designed for one size of implant, only one guide instrument being employed with them.

In order to cope with great variations in the size of the implants guide instruments of different size may be employed, the difference in size relating to the size of the cross section.

The implantation system may hence either comprise a guide instrument with one or more component sets or a plurality of guide instruments each respectively having one or more component sets or of a range of spacers and one or more component sets.

An advantageous design is one involving the combination of a spacer with a guide instrument, the guide instrument being provided at its end with detent means for cooperation with the spacer.

The system in accordance with the invention facilitates and accelerates an implantation procedure, it rendering possible in the case of the use of the elongated guide instrument also a short length of the operation incision, since the elongated guide instrument with a relatively small cross section can serve or, respectively, be designed simultaneously for the displacement of muscle tissue so that all steps in surgery take place within the elongated instrument.

During surgery the guide instrument is introduce through a relatively small incision until it abuts against the vertebrae to be treated or slips into place between them. This guide instrument serves as an access means, a holding means and a guide for the further implantation steps. Using the suitable surgical implements the cavity for the implant or implants is prepared and then, without putting down the guide instrument, the implant is introduced with an exact fit into the prepared cavity. Thereafter, possibly after the introduction of bone substance and a bone cover as closure, the guide instrument is removed again and the operation wound closed.

One possible form of the invention for rapid and accurate performance of the implantation method for the immobilization of vertebrae comprises a spacer, which is employed in connection with a spreading forceps. The spacer in accordance with the invention comprises at least two distance members, which engage the edges of the vertebrae. By means of a spreading forceps, which is simultaneously designed to function as a height measuring device, adjacent vertebrae are spread apart, the distance is measured and a spacer is selected which has suitably high distance members and inserted between the vertebrae.

An other advantageous feature of system for attaining the object of the invention is such that the implantation system comprises implants, which are provided with openings and/or ribs, which render possible anchoring of the implant to staples adapted to be driven into the bone. The implant may in this case be optimized in accordance with anatomical aspects and with rapid manipulation without having to restrict the possibilities of fixation. The staples do in fact offer a free selection as regards the arrangement of the fixing means.

Such an implant preferably is provided with guide means so that using a guide instrument and possibly a spacer, it is possible to perform positioning and insertion rapidly and exactly. Thereafter the guide instrument and any spacer is removed and one or more staples are driven in. Such a rectangular block-like implant as described above will for this purpose have openings, starting from one end, through which one limb of one or more staples extends. A U-like implant may be provided with a head connecting the free ends of the two implant limbs, such head being encircled by the staples.

Fixation by means of staples is possible for all types of conventional and novel implants for the vertebral column. Fixation using staples offers the advantage over the lugs in accordance with the said European patent publication 179 695 that no screwed joints are required and that there are many more possibilities of variation as regards the position of attachment.

The staples may be advantageously designed with a detent action, the limbs of such detent means being thrust around the head on being slipped thereover and then coming together again as soon as the narrow part has cleared the head. It is in this manner that tension between the staple limb and the bone is caused to act to improve anchoring of the staples on the bone. Furthermore a secure attachment of the staples on the head of the implant is ensured.

For anchoring known two- or multi-limbed, wire or broad band staples may be employed (see the said German patent publication 3,310,835 and the British patent publication 2,017,502). More particularly it is possible to utilize a three-limbed staple in conjunction with a two-limbed one, the intermediately arranged staple being threaded through a central recess in the bent part of the three-limbed staple. The two staples are driven into one respective adjacent vertebra. The lengths of the staple limbs are not the same when the staples are driven in obliquely, because when they have reached the bone they have to move through different distances.

An other feature of the invention is such that the staples are provided with a preparatory spike and a staple holder. Both implements are S-shaped and are forked at one end thereof. The other end is adapted to receive a ramming implement.

The ramming implement is so designed at the free end with an abutment shoulder that it serves both as a ramming means and also, in connection with a suitably designed hammer, as a removing implement. In the latter case the ramming implement is screwed onto a forceps for positioning implants in a backward direction. The abutment shoulder is, in accordance with a design which is simple to manufacture, an annular shoulder, which is designed in the form of a screwed on, bonded cap. For this purpose a claw hammer i. e. one with a slot, is suitable, which fits around the ramming implement.

The forked end of the preparatory spike can be provided with two or more spikes, which are able to be driven into the bone of the vertebra. It is into such prepared holes that the staple is driven by means of the staple holder later. The S-shaped configuration of such implements renders possible freely selectable positioning without interfering with adjacent parts of the body such as the thorax or head and the staples may be driven with any desired alignment thereof into the vertebral bone.

The surgical implement set for the implants as described may with advantage additionally include a very simply designed height measuring and spreading device for the gap between vertebrae. The height measuring device may consist of two pivotally connected, arcuate rods, in the case of which at one end the red ends are provided with measuring surface for engagement with the adjacent vertebrae. At the other end of the height measuring device the rod ends are provided with a measuring rod.

Further advantageous developments and convenient forms of the invention will be understood from the following detailed descriptive disclosure of embodiments thereof in conjunction with the accompanying diagrammatic drawings.

FIGS. 1A–B shows a guide instrument.

FIG. 2 shows the cross section of a further guide instrument.

FIGS. 3 and 4 respectively show a surgical implement.

FIG. 5 Shows a cross section taken through the implement of FIG. 4.

FIGS. 6–8 respectively show one implant.

FIGS. 9 and 10 respectively show one working embodiment of the use of staples for securing an implant in position.

FIG. 11 shows a guide instrument with a spreading device.

FIGS. 12a, 12b and FIGS. 13a, 13b respectively show an implement for staples.

FIGS. 14 and 15 respectively show a bone press.

Figure 19A:
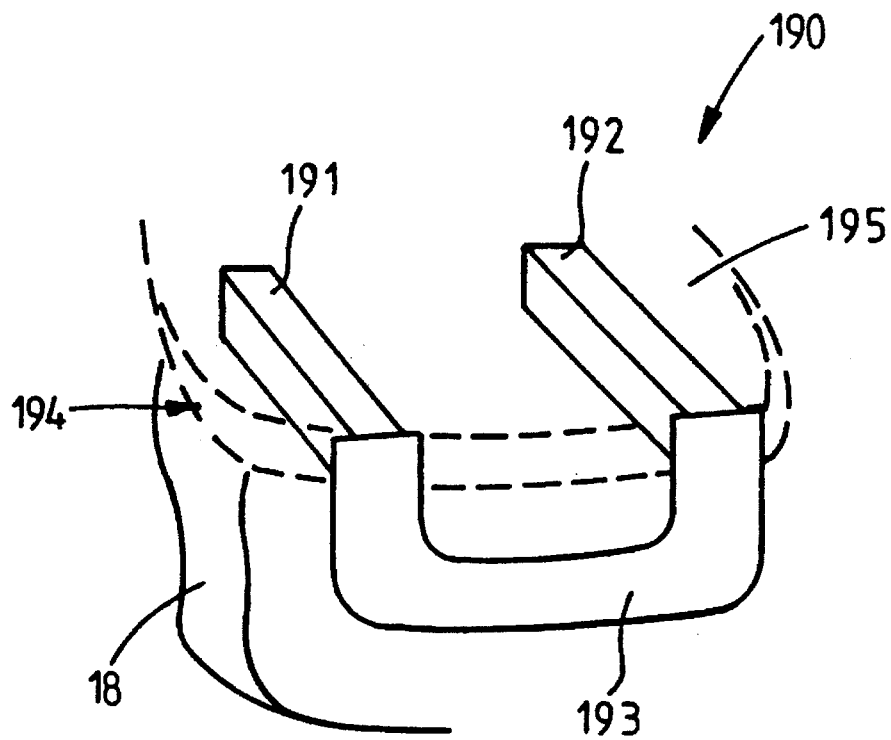
Figure 19B:
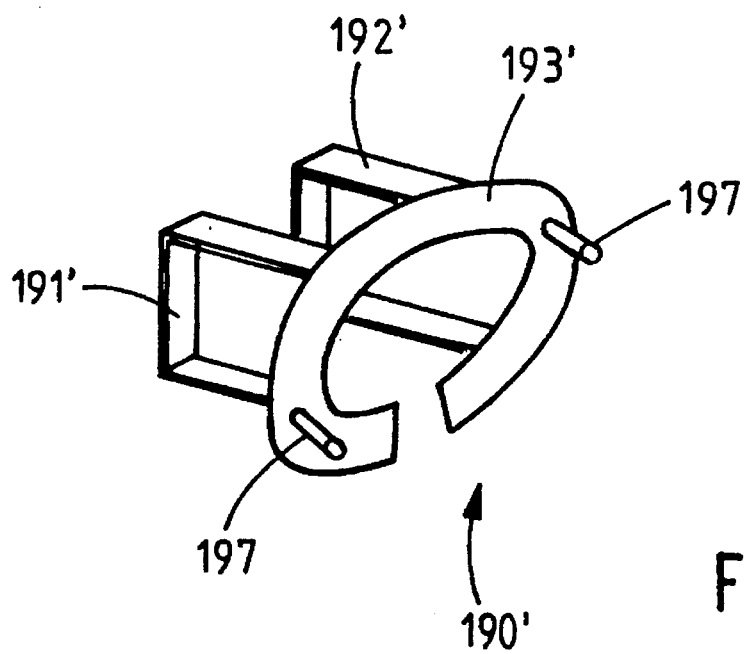

FIGS. 19a and 19b each show a spacer.

DETAILED ACCOUNT OF WORKING
EMBODIMENTS OF THE INVENTION

Figure 1:
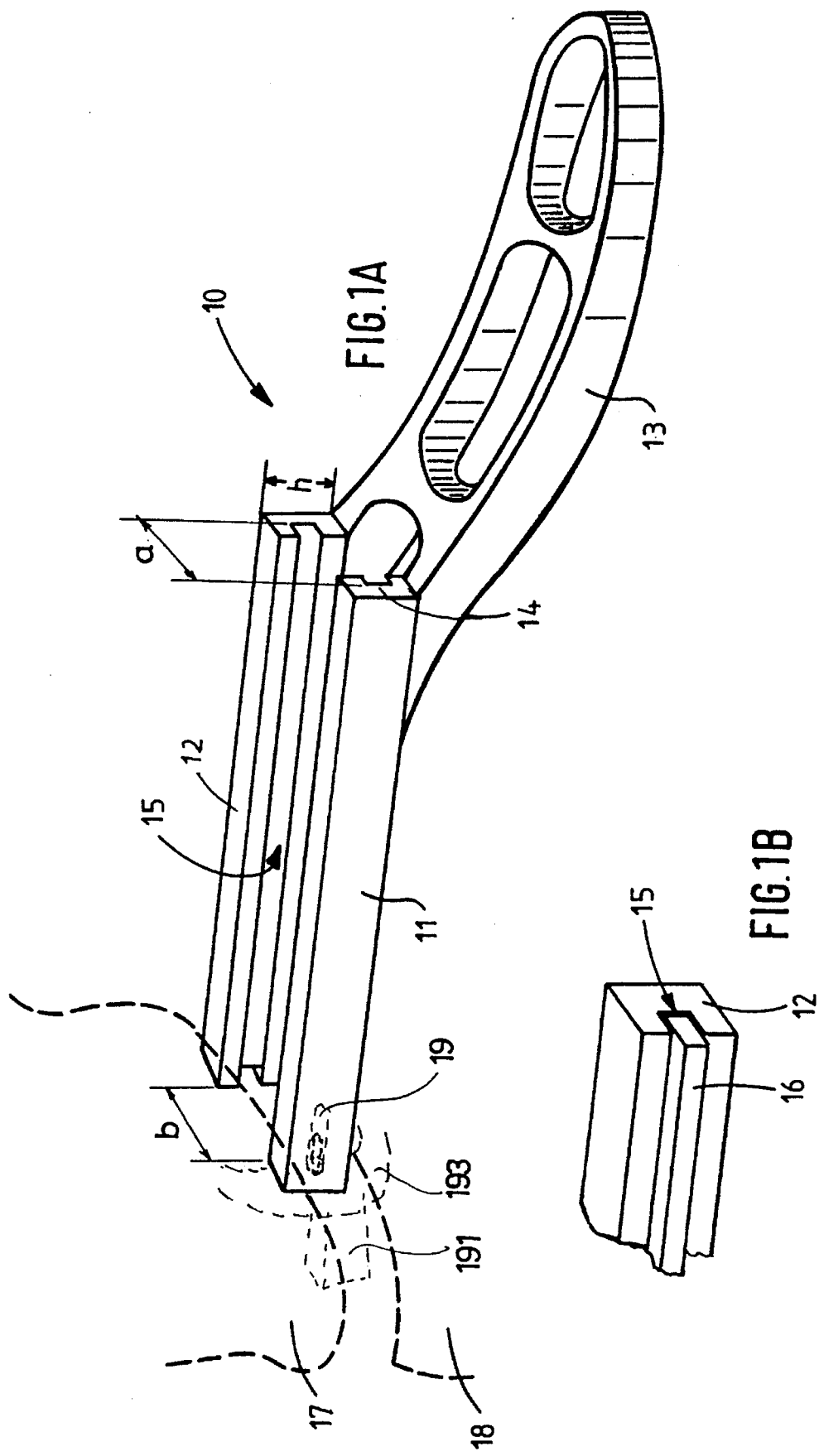

FIG. 1 shows an auxiliary device, designed in the form of a guide instrument 10, for the insertion of implants for the immobilization of vertebrae, and comprising as its main parts two guide rails 11 and 12, which are aligned in parallelism to each other and are fixedly connected with a handle 13. The guide rails 11 and 12 are in the form of elongated rectangular blocks each with a respective longitudinal groove 14 and 15 in the opposite sides of the guide rails 11 and 12. The longitudinal grooves 14 and 15 serve for the guidance of surgical implements and implants, which respectively possesses guide keys adapted thereto.

The instrument 10 in accordance with FIG. 1 composed of the two adjacently arranged guide rails 11 and 12 in accordance with FIG. 1 can be made with such a height h that it is able to be introduced into the gap between two adjacent vertebrae 17 and 18. The free space available at the top or at the bottom between the guide rails 11 and 12 renders possible the introduction of surgical implements or implants with different heights, that is to say implements and implants made with a constant width dimension a matching the guide keys and limited in the other width dimension b. However here as well differences in size may be taken into account, if it is expedient or desired, something which is readily made possible by the inserts able to be put in the longitudinal grooves 14 and 15. FIG. 1b for instance shows an insert designed in the form of an elongated rectangular block 16, which converts the guide groove 15 into a guide key 16, this simultaneously providing for a change in width if required. If an implement, as for example a drill (used to produce a cavity with a small width in the vertebrae) takes up the full width b of the guide instrument 10, the guide grooves 14 and 15 will then be employed. The implant to be mounted in the cavity on the contrary will not occupy the full width b of the guide instrument 10. In order in such a case not to have to provide high guide keys on the implant, the surgeon will either reduce the size of the groove spacing a with a suitable insert or, as shown in FIG. 1, form keys 16, which are able to cooperate with corresponding grooves in the implant.

It is in this manner that one and the same guide instrument 10 may be fitted with guide grooves 14 and 15 (see FIG. 1a) or with guide keys 16 (see FIG. 1b) and for different widths a and b. It is naturally possible to design the guide rails 11 and 12 to be integral with the guide keys.

The instrument depicted in FIG. 1 and composed of guide rails 11 and 12 is extremely simple to manufacture and requires but a small amount of space during surgery. The guide instrument 10 is suitable for ambulant implantations, in the case of which all surgery is performed through a previously introduced tube which holds back tissue. It is through this tube that the guide rails 11 and 12 can be moved as far as the vertebrae 17 and 18.

Figure 2:
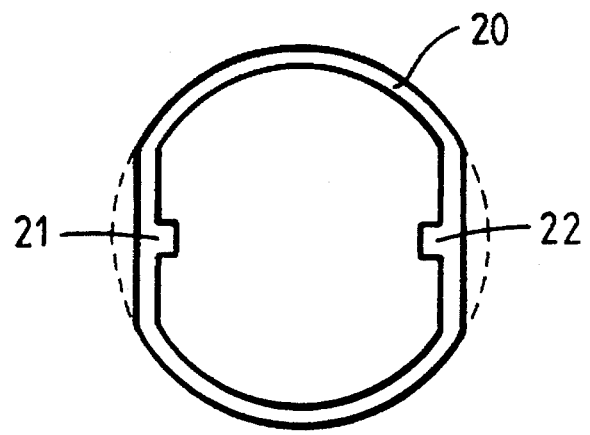

The invention further contemplates cases in which the tube assumes the guide function, that is to say that the guide instrument for the implantation is not as in FIG. 1 in the form of rails, but rather as a practically closed tube 20. FIG. 2 shows the cross section of a tubular guide instrument. Within the guide tube 20 two guide keys 21 and 22 are provided, which cooperate with corresponding guide grooves on the implements and implants. It will be obvious that other cross sections of the guide instrument are possible to the extent that the same are in line with anatomical and manufacturing requirements. The external periphery is cylindrical and can be provided with flats as shown in FIG. 2.

Figure 3:
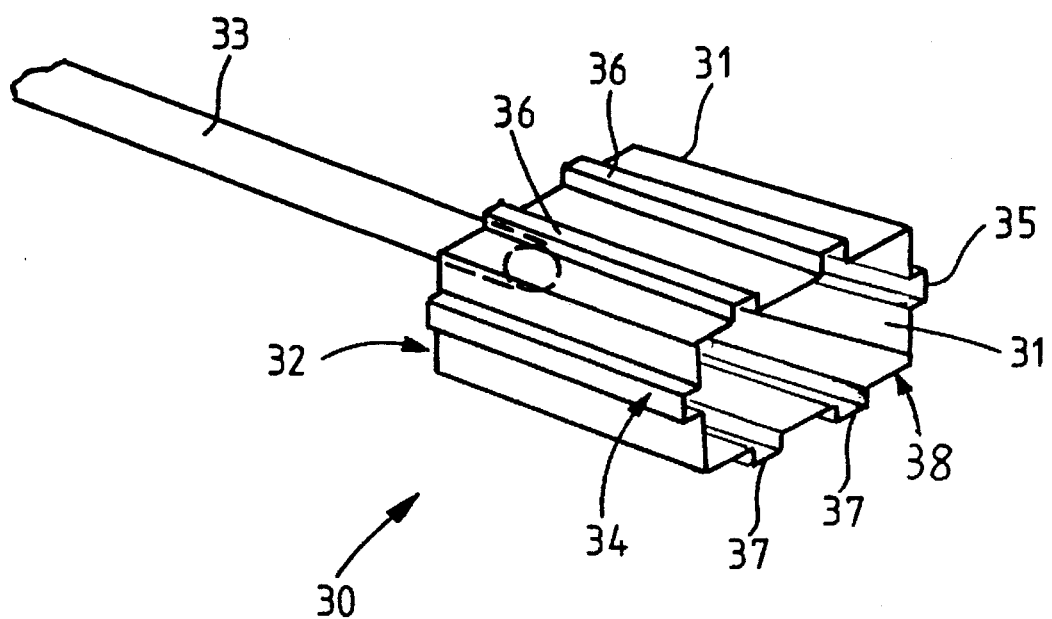

FIG. 3 shows a stamping implement 30 designed for cooperation with the guide instrument 10 in accordance with FIG. 1 and serving as a chisel, which is designed for the excavation of a cavity with a polygonal cross section. The stamping implement 30 comprises a tubular chisel 31 with a rectangular cutting edge 38 at one end thereof whereas the other end 32 is closed. The closed end 32 bears an impact rod 33. On the lateral surfaces of the chisel 31 guide keys 34 and 35 are formed, which fit into the guide grooves 14 and, respectively, 15 of the guide implement 10.

In the case of the stamping implement 30 illustrated in FIG. 3 in the upper and lower sides of the chisel 31 longitudinal keys 36 and 37 are also formed. It is with these keys 36 and 37 that corresponding grooves are cut into the vertebrae 17 and 18 which serve to reliably position and hold a correspondingly designed implant. The configuration of the upper and lower surface of the chisel 31 is without influence on the design of the guide instrument 10, more particularly since the guide rails 11 and 12 thereof come to be connected with the lateral surfaces of the chisel 31.

Figure 4:
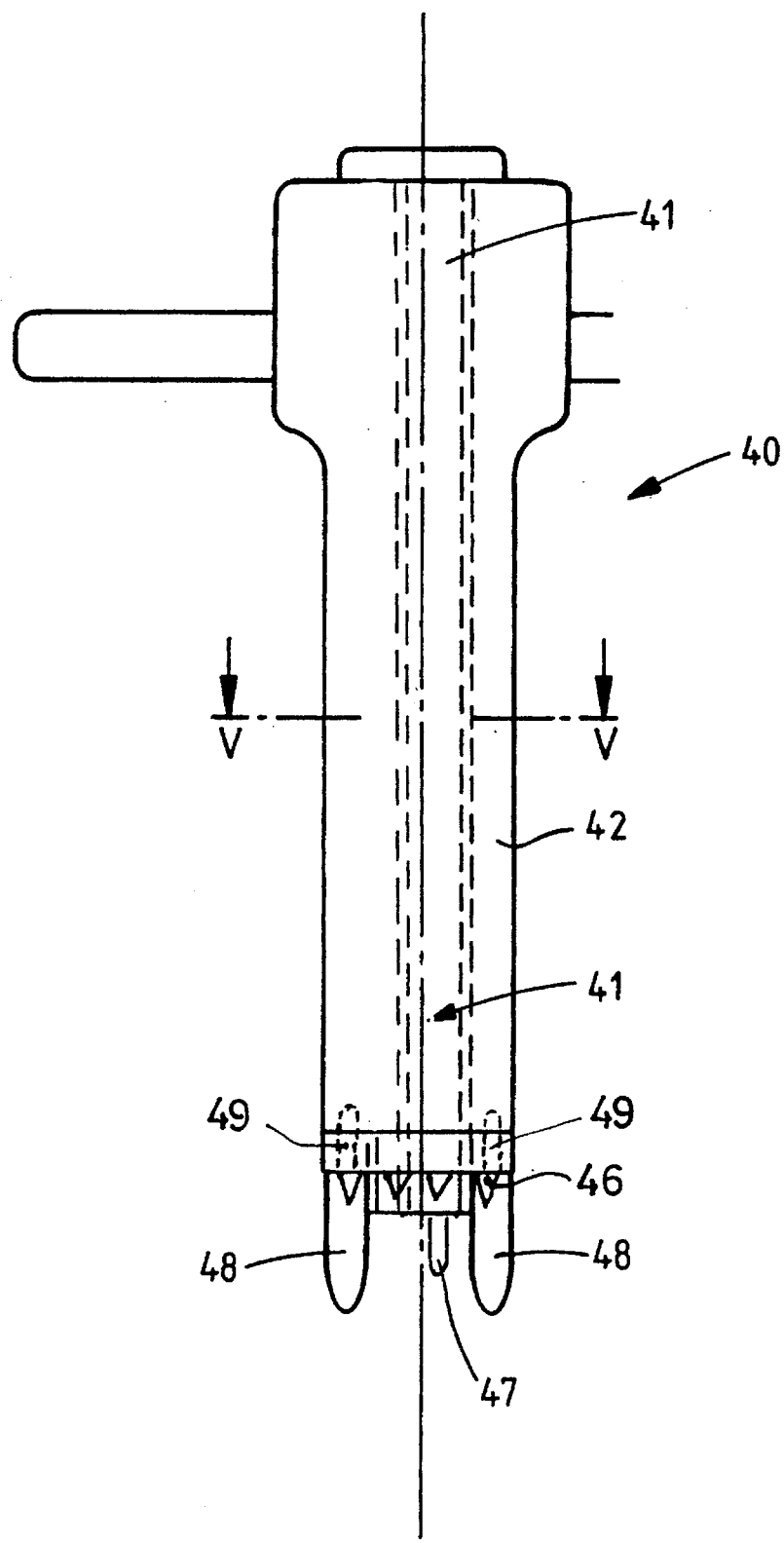
Figure 5:
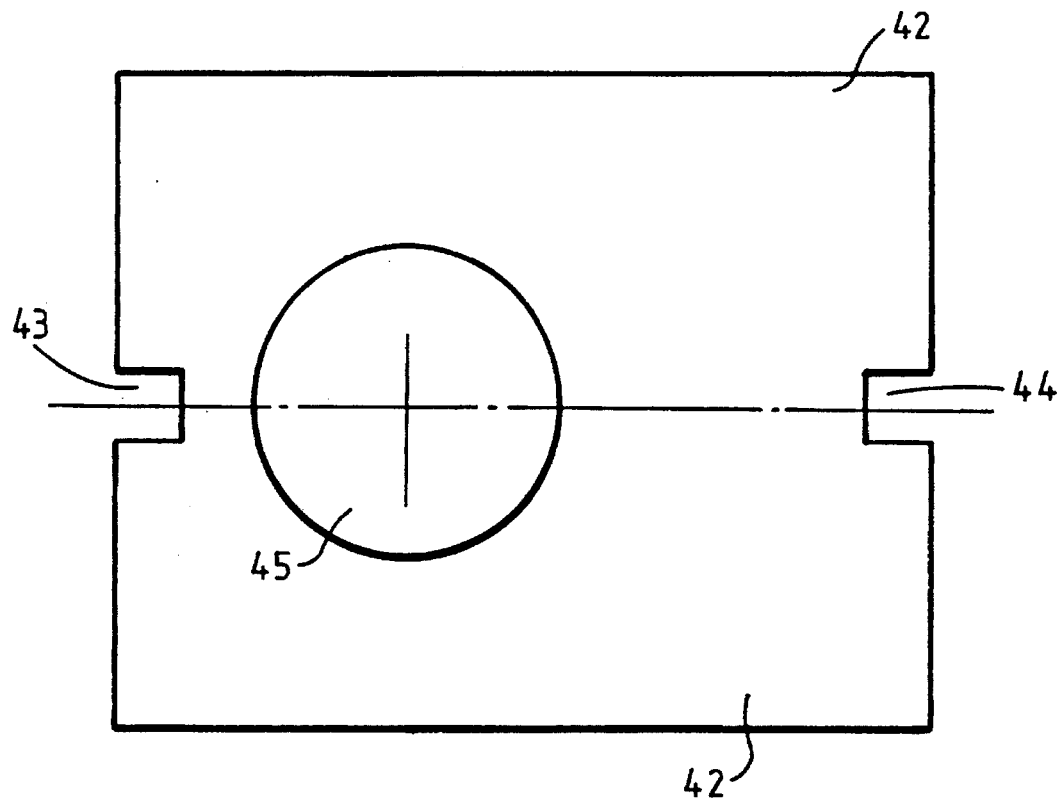

FIG. 4 shows a further implement 40 provided for producing holes and which comprises a drill insert 41, which mounted for cooperation with a guide instrument 10 or 20 in a housing 42, which, as shown in FIG. 5 in cross section in more detail is provided with lateral guide grooves 43 and 44, which cooperate with keys 16 or 21 and 22 of the guide instrument. The housing 42 possesses an eccentric longitudinal hole 45, in which the drill insert 41 is bearinged with the drill 47. This design is suitable for producing two holes close together by mounting the drilling implement 40 once pointing in one direction and once pointing in the opposite direction i. e. with an offset of 180° into the guide instrument. Likewise the invention contemplates the mounting of a hollow routing tool or other milling cutter, if the guide is designed in the form of a long shaft.

The housing 42 possesses two distance pins 48 on the side adjacent to the drill, which are able to be mounted on the guide instrument 20 as well and which are inserted into the free space between the vertebrae in order to be able to position the guide instrument perpendicularly to the vertebra's axis and not to tilt. Furthermore locating pins 46 are provided which bite into the bone.

The surgical implement in accordance with FIG. 4 and furthermore the guide instrument in accordance with FIG. 1 may however also be employed with a spacer, which is illustrated in FIG. 19 and is described infra. For this purpose detent means are provided at the end of the surgical implements and of the guide instrument, such detent means cooperating with corresponding complementary means on the distance member in order to fix the implement in the field of surgery exactly for surgery (drilling, chiseling, insertion of the implant). In the case of a simple arrangement the detent means comprise at least two recesses or drilled holes 49 and 19, which cooperate with humps or, respectively, pins 197 on the spacer 190'. FIG. 19 illustrates spacer 191 and 193 in broken lines.

It would furthermore be possible for the guide instrument to be provided with spreading means, which after introduction of the instrument would be drawn apart in order to increase the gap between two adjacent vertebrae 17 and 18. An example of this is described further below in conjunction with FIG. 11.

For surgery the guide instrument is brought into engagement with the terminal surface of the vertebra to be treated and secured by means of locating pins driven into the bone substance. Then a cavity is prepared for the implant. For this purpose firstly an implant is introduced through the guide instrument for drawing off the vertebral disk by suction. Dependent on the configuration of the implant to be inserted the bone handling surgical implement in the form of a drill, chisel or the like is employed and guided by the instrument in order to mill out bone substance. The result will then be a cavity which is exactly positioned in its configuration in relation to the guide instrument. Bone substance shavings produced will be drawn off by aspiration. Then—if required—a test implant of metal with the same configuration as the cavity and the final implant will be inserted in order to be able to check the position thereof intraoperatively by means of a diagnostic device.

A test implant is necessary in cases wherein the final implant consists of synthetic resin and does not comprise any x-ray contrast material. After checking and performing any improvements necessary of or in the position of the cavity the implant as such—possibly guided by means of the instrument—is introduced into the exactly shaped cavity.

In order to produce a spreading action the height of the cavity is made less than the height of the implant. In this case the implant is driven in with a ramming implement. In order to ensure an even application of driving force the ramming implement, like the other surgical implements, is guided in the guide instrument. In this respect a conical design of the implant may be of advantage.

Figure 6:
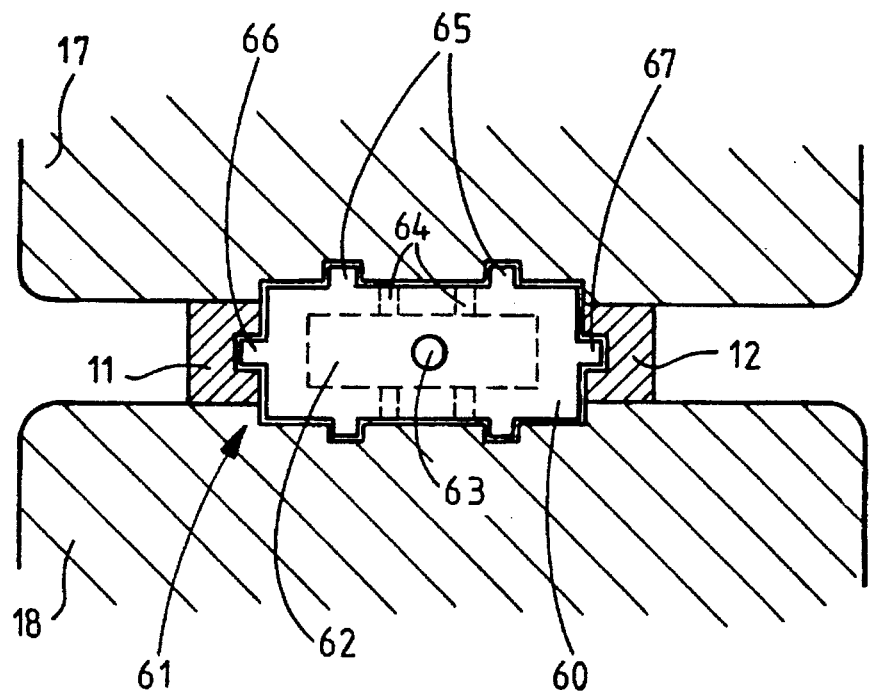

FIG. 6 shows the completion of immobilization of two vertebrae 17 and 18 in a longitudinal section of the vertebral column. Between the vertebrae 17 and 18 there are still the free ends of the guide rails 11 and 12. In the intermediate space between the two guide rails 11 and 12 an implant 60 has been introduced into a cavity 61, which was previously excavated using a stamping implement 30 (FIG. 3). The implant 60 is a rectangular block-like component with a cavity 62 in it, into which bone substance may be introduced via an opening 63. Through holes 64, which extend through the lower wall of the implant 60, the bone substance comes into contact with the vertebrae 17 and 18 so that coalescent growth between the vertebrae 17 and 18 is possible. Any unevenness 65 on the contact surface between the implant 60 and the vertebrae 17 and 18 will serve for securely anchoring the implant 60 between the adjacent vertebrae 17 and 18. The configuration of the unevenness 65 is taken into account even during the production of the cavity 61 using the respective implement, in this case the stamping implement 30. The implant may also consist of resorbable material if its initial supporting action is to be later assumed by the bone substance.

After the insertion of the implant 60, which is able to be introduced into the prepared cavity with the aid of the guide keys 66 and 67 and the guide rails 11 and 12 extremely readily and exactly, the guide instrument 10 is removed from the site of surgery.

Figure 7A:
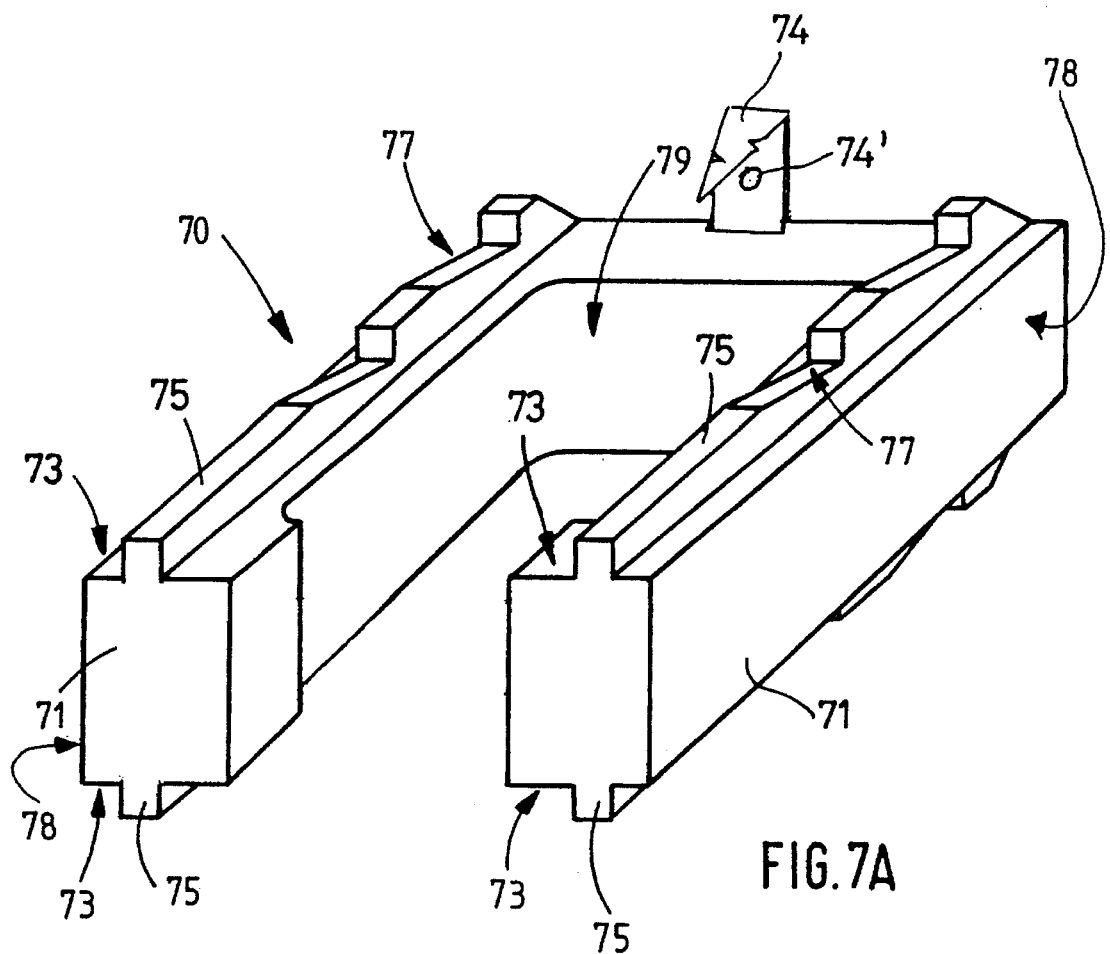

In FIG. 7a another example of an implant 70 is illustrated which is more especially suitable for the immobilization of cervical vertebrae. The implant 70 comprises a U-shaped structure, whose limb 71 has roughness at a surface 73 cooperating with a vertebra, such roughness being in the form of a longitudinally directed key 75, which simultaneously may serve as a guide key means. The guide keys 75 lead to a reliable lateral anchoring of the implant 70. In order furthermore to provide reliable anchoring in the sagittal plane, the keys 75 may possess notches 77, into which bone substance may grow invasively. Such notches may for instance also be provided on the roughness 65 of the implant 60.

For the implant 70 depicted in FIG. 7a a tubular instrument or an instrument consisting of guide rails is necessary, which has four guide grooves, which cooperate with the guide keys 75 of the implant 70. The guidance may be furthermore arranged to take place on the sides 78 of the implant 70.

In FIG. 7a an example is illustrated in the case of which the external sides 78 of the limbs 71 each have a guide groove 76 therein, which render it possible for a guide instrument to be employed in accordance with FIGS. 1b or FIG. 2. The intermediate space 79 between the limbs 71 of the implant 70 may be filled with bone substance. The bone substance may preferably be thrust into the intermediate space 79 by means of a bone press 140 or 150 (FIGS. 14 and 15) prior to insertion of the implant 70 into the intermediate space. Using a press with a suitable geometry it is possible for the setting of the quantity of material and the filling operation to be quickly and reproducibly performed. Introduction of the bone substance in the implanted condition is on the contrary a tedious process. Working examples of bone presses will be described in connection with FIGS. 14 and 15.

The above described implants are all of the same height but have difference side angles or slopes (that is to say the implants are wedge-shaped) in order to be able to perform a spreading operation and the physiological segment curvature is restored.

For this purpose in the site of surgery at the vertebra a cavity is prepared, whose constant cross section corresponds to a value between the minimum cross section to the average cross section of the implant. The implant is then inserted by impact between the vertebrae. This process is, as mentioned supra, performed within and through the guide instrument.

A lateral tension or biasing action between the implant and the bone may also be produced for reasons of secure fixation. The U -shaped implant may for instance be introduced with a biasing effect by thrusting together the limbs 71. The resulting enhanced high degree of friction produced between the implant and the bone will aid in providing a reliable anchoring effect for the implant.

The above described implants essentially possess a rectangular cross section. It is however obviously possible to utilize implants which possess a more or less circular cross section, and which have guide means extending along the generatrices. An example is depicted in FIGS. 8a and 8b.

Figure 8A:
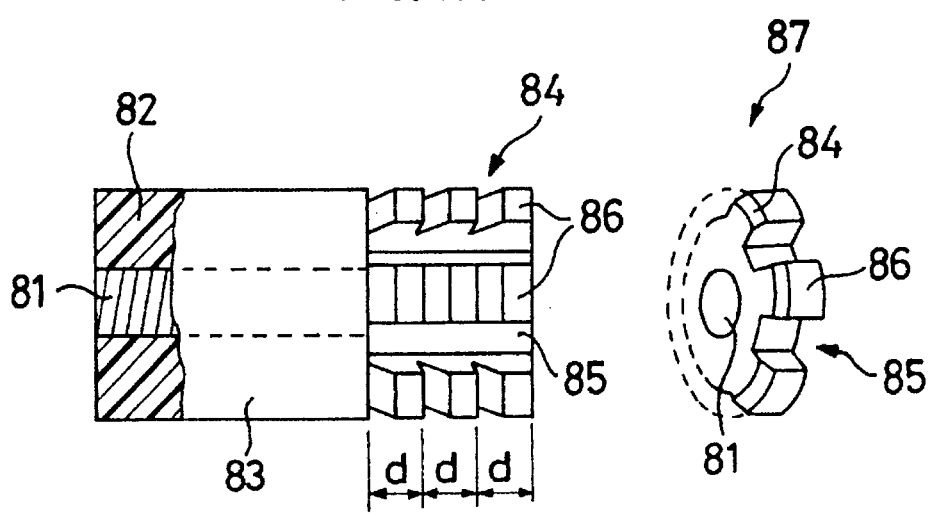
Figure 8B:
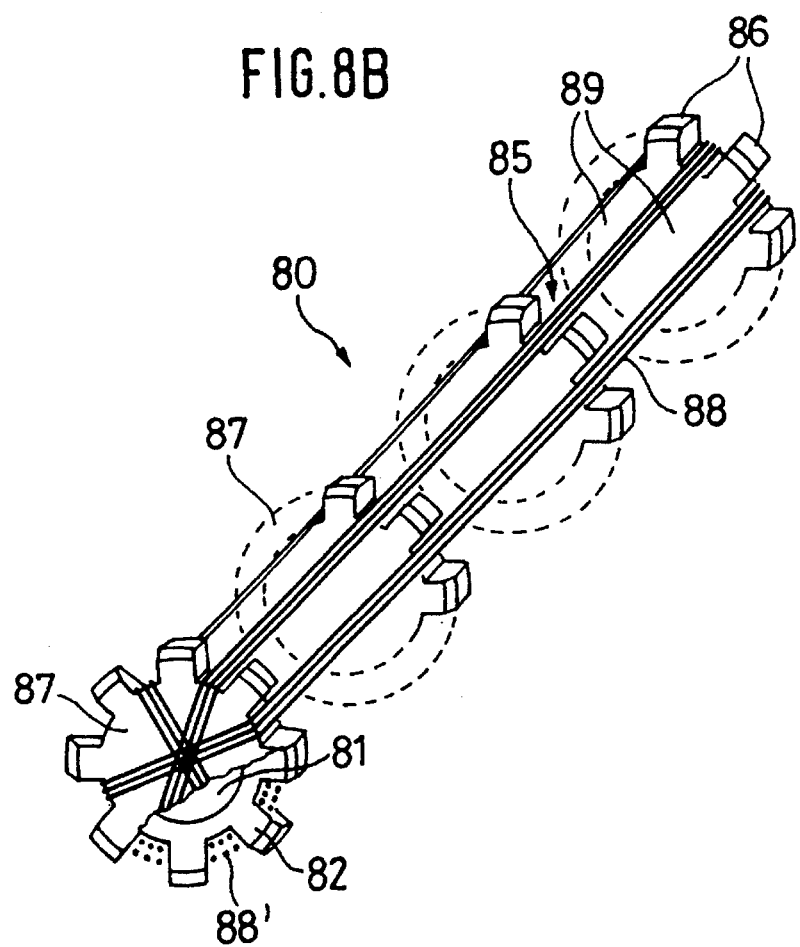

In FIGS. 8a and 8b various different methods of manufacturing a cylindrical cage-like implant 80 are depicted. A cylindrical core 81 is surrounded with a plurality of braided layers 82 or has a plurality of crossing layers wound onto it. On the cylinder 83 so produced notches 84 are machined at regular distances d apart extending in the peripheral direction whereas in the longitudinal direction grooves 85 are produced by grinding so that the external periphery of the cylinder 83 possess a multiplicity of teeth 86. The cylinder 83 is then cut up into disks 87 with a thickness d to constitute supports for the cage-like implant 80.

As shown in FIG. 8b in more detail, the support disks 87 are positioned at predetermined, regular distances apart on a thin steel mandril, not illustrated, in order to have UD fiber 88 wound on them. The UD fiber layers 88 are wound into the grooves 85 between the teeth 86 along the longitudinal axis of all support disks. The layers of UD fiber are wound as far as a position underneath and short of the teeth 86 so that the teeth 86 with the oblique surface 84 serve simultaneously as an anchoring means and as a guide means in the implantation instrument. The internal space in the implant is filled with bone substance so that growth of bone from the one vertebrae, through the intermediate spaces 89 between the UD fiber bundles 88' and to the other adjacent vertebrae will be possible.

The implant 80 in accordance with FIG. 8a and FIG. 8b which constitutes an embodiment of a cage-like implant, may be produced in a winding method which is simple from the point of view of manufacturing technology and possesses the advantage of comprising fibers which are under tension and are aligned in a predetermined manner. Such an implant 80 is more especially suitable for immobilization of lumbar vertebrae.

Figure 9:
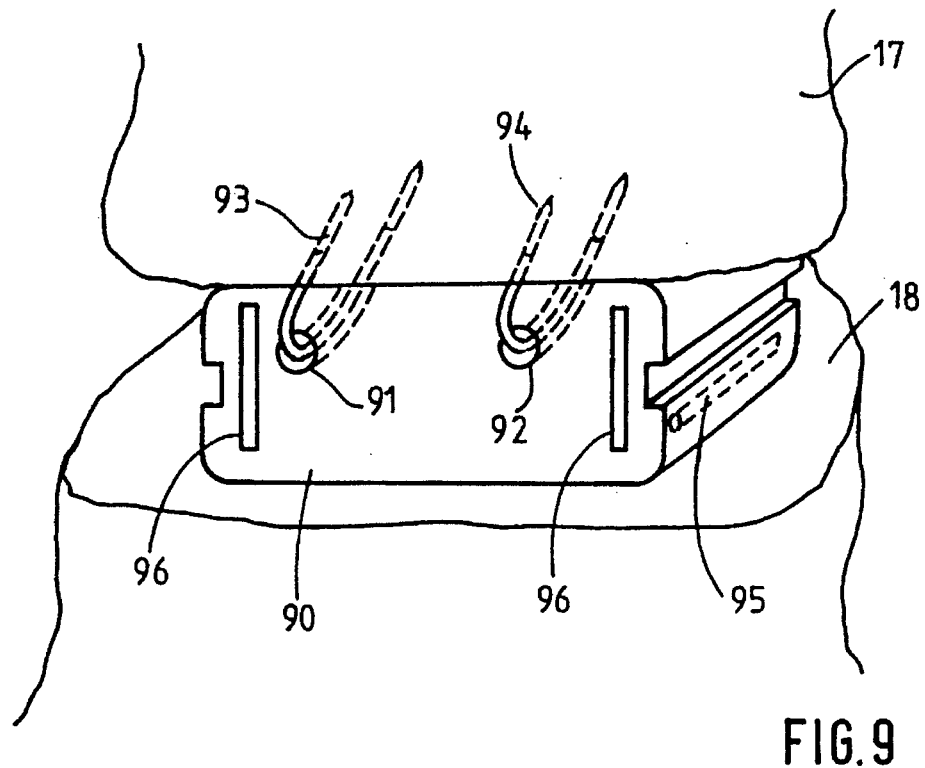
Figure 10:
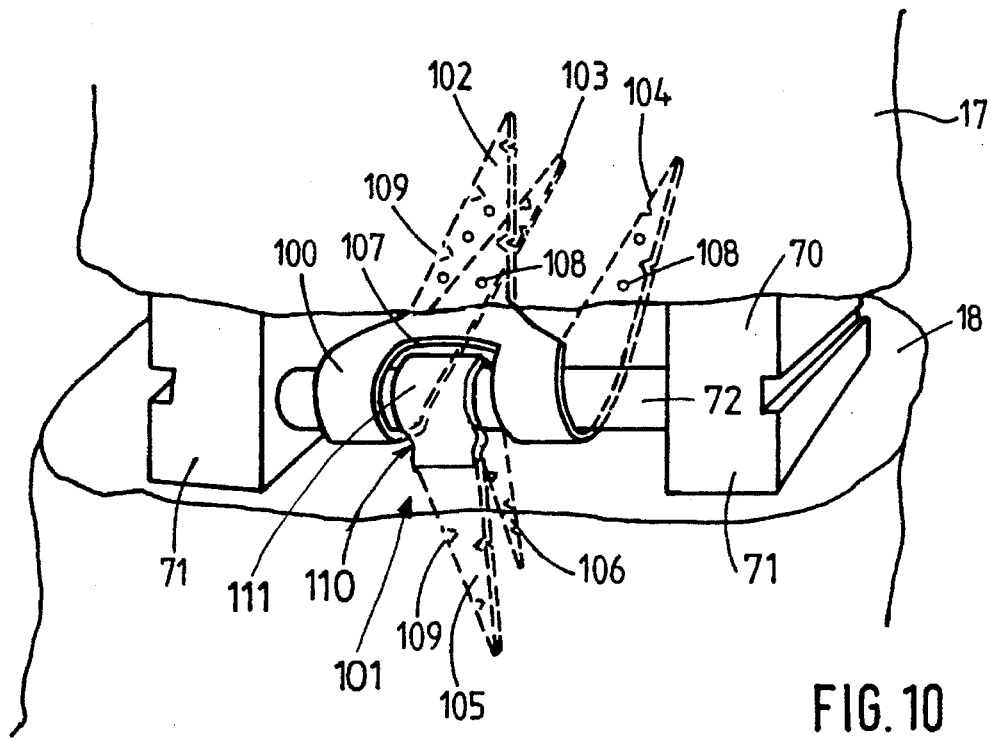

FIGS. 9 and 10 show two examples for securing the implants in the first stage of the operation by means of staples.

FIG. 9 shows two vertebrae 17 and 18 after immobilization using a rectangular block-like implant 90. The openings 91 and 92 located at the upper end of the implant 90 have a respective limb of a hair-needle-like wire staple 93 and 94 threaded through them. The staples 93 and 94 are obliquely driven through the adjacent upper vertebra 17 and possess limbs of different length in order to ensure a equal depth of penetration into the bone. The lower limb has to extend through a longer free space as far as vertebral bone 17 so that such limb is longer than the other one.

Figure 7B:
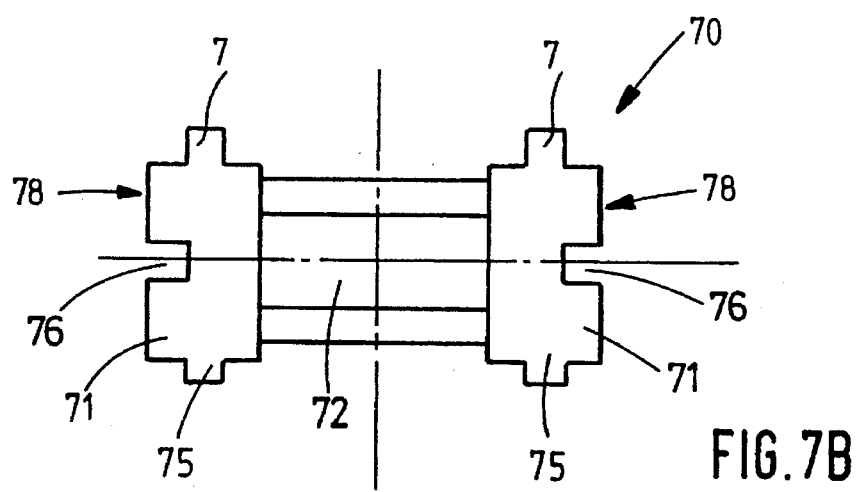

FIG. 10 shows an example with two interlocking staples 100 and 101, which are manufactured from bent, broad bands. Such staples 100 and 101 are more especially suitable for open implants which have a head or which may be provided with a separate head for the staples. The U-shaped implant 70 in accordance with FIGS. 7a and 7b is an example for this. For the staples 100 and 101 a separate staple head 72 is provided connecting the implant limbs 71 and around which the stales 100 and 101 extend. The one staple 100 has three limbs (limbs 102 through 104) and so designed with a central opening 107 in the arcuate part that a second staple, arranged between the limbs, in this recess 107 may fit around the head 72. The layers 102 through 107 run together at an acute angle and have holes 108 and furthermore lateral notches 109 to promote coalescent growth with the bone. The upper individual limb 102 of the three-limbed staple is made shorter than the two lower limbs 103 and 104, which have a longer path to the vertebra 17.

The staple 101 additionally possesses a detent function. It has a constriction 110, by which the limbs 105 and 106 are spread apart on driving in the head 72 and in the spread apart state penetrate the bone. After moving past the constriction 110 it closes partly again with a detent action so that the head 72 remains trapped in the arcuate part 111 of the staple 101. The limbs 105 and 106, which spring back, are consequently, together with the bone, acted upon by a mutual compression force, something which serves to promote anchoring of the limbs on the bone.

In the case of the embodiment of FIG. 10 the one staple 100 is attached inside the upper vertebra 17 and the other one is attached in the lower vertebra 18. Combinations of staples of different configuration and in different arrangement are also contemplated by the invention. The implant in accordance with the invention may furthermore be fitted with integral staples. In FIG. 7a an integrated staple 74 is depicted which is either directly driven in or is able to be attached by means of screws. The screw is run through the hole 74' provided in the integrated staple 74.

An implant of this type may readily be employed with an integrated staple 74 in the same guide instrument 20.

The above described part for the immobilization of vertebrae may with advantage be produced and marketed as an instrument system or set. Such system would comprise a guide instrument, for example 10 or 20, one or more insert pairs 16 for changing the guidance width or, respectively, type of guiding action, surgical implements such as drill sets, suction sets, chisels and impact implements and furthermore a set of implants with guide means and, possibly, the respective staples. The implantation system renders possible a rapid and accurate immobilization of vertebrae anywhere along the vertebral column.

The immobilization 60 and 70 the staples 90 and 95 and the guide instrument are preferably manufactured of fiber reinforced synthetic resin. In order to localize the implants which have been inserted the same contain contrast material. For this purpose use is made of rods 95 and 96 of a material which is not transparent to x-rays, as for instance metal or barium sulfate, which, as indicated in FIG. 9, are located in the implant 95 or in the surface 96 thereof in a predetermined arrangement. However in the case of synthetic resin implants in accordance with the invention x-ray contrast materials are not absolutely necessary. The system in accordance with the invention renders possible convenient handling of problematical implant of metal, which are inserted in the prepared bone cavity only in order to check a position.

The guide instrument may furthermore be fitted with a spreading device, with which, after the introduction of the free end of the guiding instrument, the two adjacent vertebrae 17 and 18 are spread apart.

Figure 11:
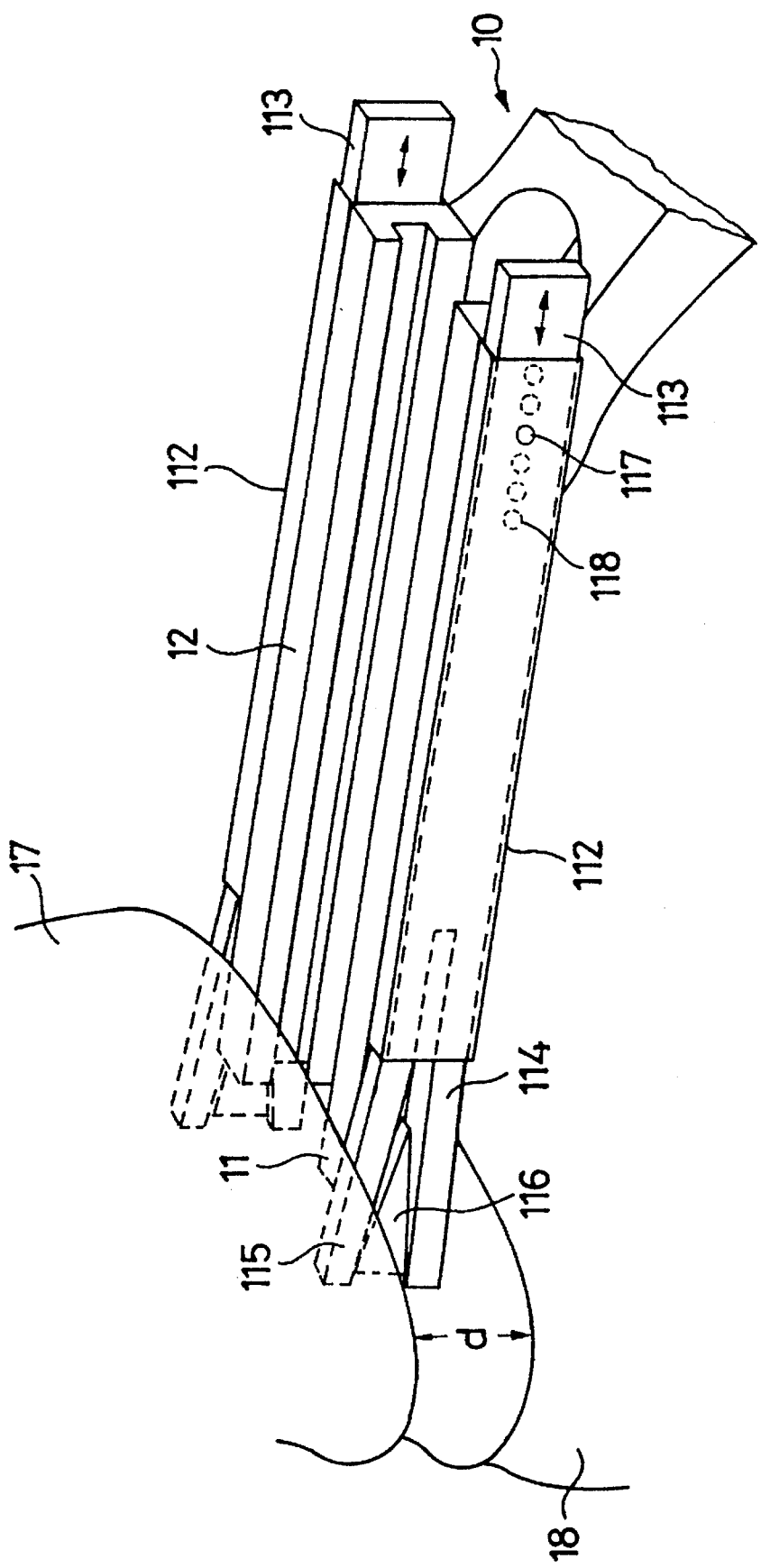

FIG. 11 shows an example in conjunction with the guiding instrument 10 in accordance with FIG. 1a. The spreading device comprises two rods 113, which are able to be respectively slid longitudinally in a guide passage 112 and which respectively have one end extending between the vertebrae 17 and 18. This end of the rod 113 is separated in the longitudinal direction into two spreading elements 114 and 115, which are urged apart by means of a wedge 116 arranged between them against the vertebrae 17 and 18, when the rods 113 are moved within the guide passage 112 toward the vertebral column. The guide instrument, which bears the guide passages 112, is in this case held fast in its position for surgery to take place. In the terminal position the rod 113 is locked with the guide instrument. For this purpose a hole 117 is provided in the guide passage, through which a pin is introduced into one of a series of holes 118 in the rod 113 so that the relative position between the spreading rod 113 and the guide instrument 10 is locked and set.

Figure 12A:
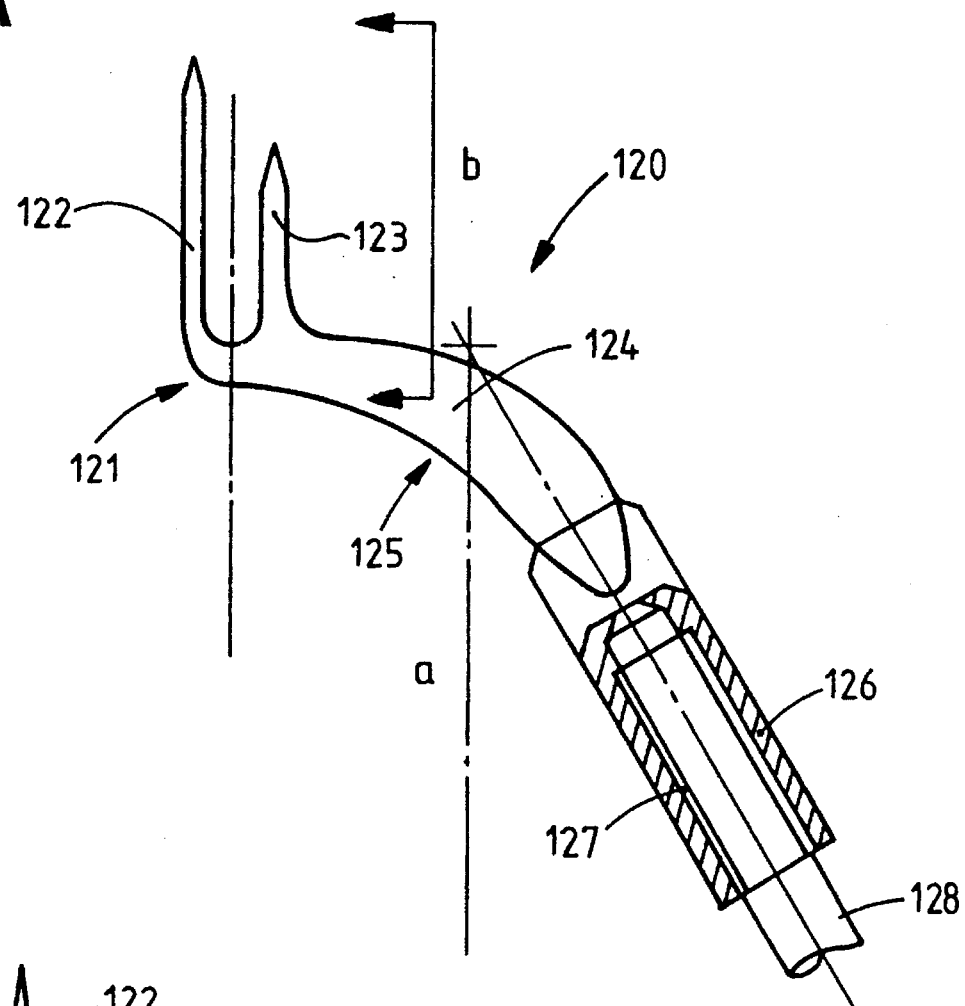

In order to be able to more readily insert the staples, which may more particularly depart from the simple wire form (in accordance with FIG. 9), it is possible to provide a preparatory instrument in accordance with FIG. 12. For anatomical reasons the preparatory instrument 120 is S-like in form, it having an end 121 bent through approximately 120°. On this end spikes 122 and 123 are provided at a right angle to the rest of the elongated part 124 of the instrument, whereas the second limb 125 of the letter S is bent in a curve in such a manner that the free end 126 extends approximately in parallelism to the spikes in order to transfer driving forces used for insertion to the spikes.

Figure 12B:
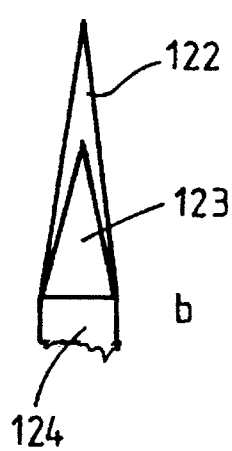

The spikes 122 and 123 serve to prepare holes in the vertebrae, into which the limb of staples are then driven. They may have the configuration of a pointed pin or be adapted to the staple limb which is to be driven in. For an adaptation to the staple 101 in accordance with FIG. 10 in accordance with FIG. 10 the spikes 122 and 123 would be triangular as viewed from the side (view b), as is illustrated in FIG. 12b.

The free end of the elongated instrument part 124 possesses a screw threaded hole 127 in order to receive a ramming instrument 128.

After the insertion of the implant (for example in accordance with FIG. 10) the guide instrument 10 is removed and the preparatory instrument 120 is applied with the spikes 122 and 123 directed downward fitting around the head 72. By blows on the ramming instrument 128 the spikes 122 and 123 are driven into the lower vertebra 18 and then withdrawn again. Using a suitable preparatory instrument having three spikes the holes in the upper vertebra 17 are produced for the second staple 100. Such surgery may be performed simply and rapidly through the passage, holding back the body tissues, to the site of surgery.

Figures 13A, 13B:
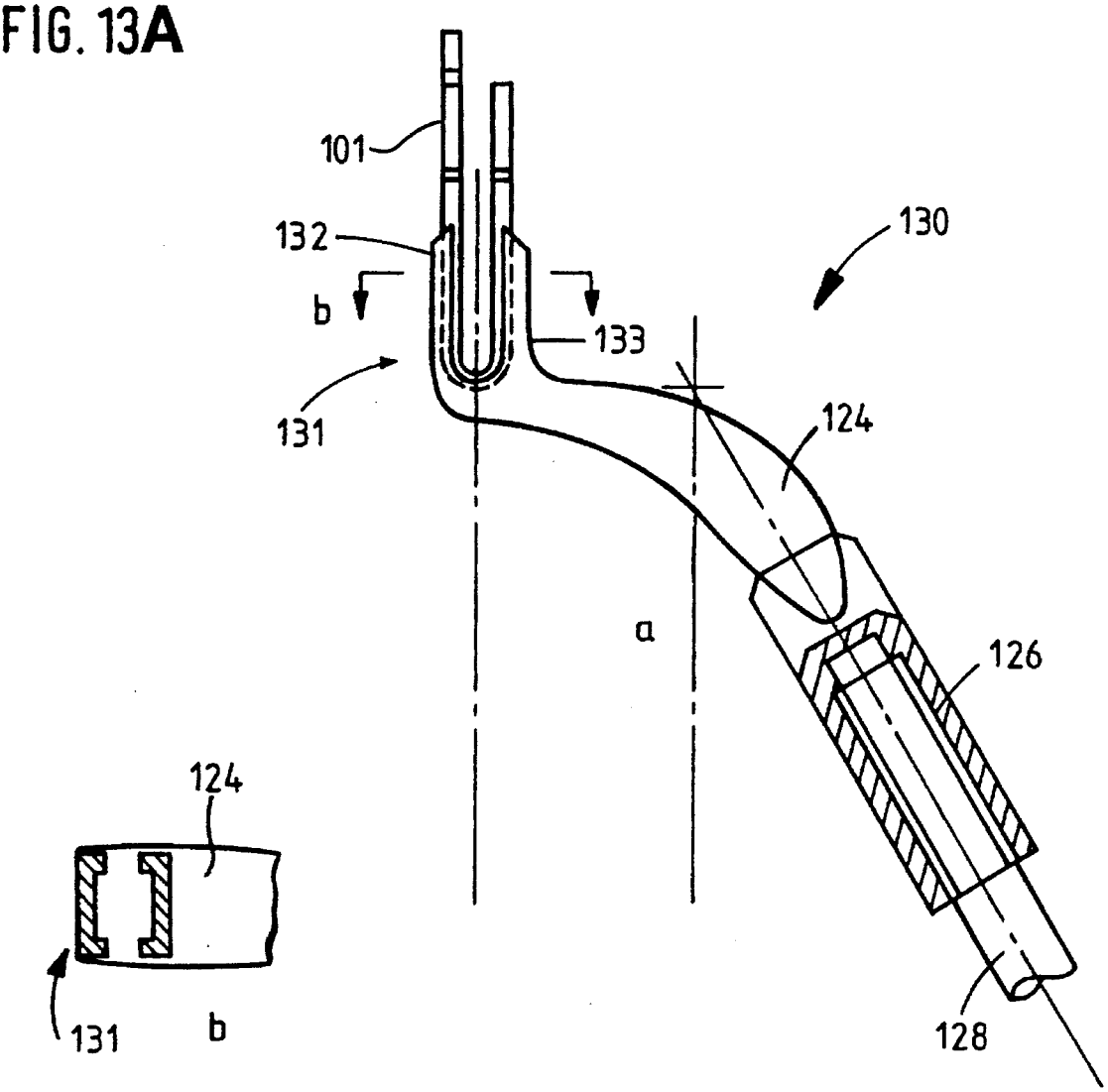

After this it is possible for the staples 100 and 101 to be introduced just as readily with the aid of a holding means in accordance with FIG. 13. The staple holding device 130 has an S-shaped form like the preparatory instrument 120. There is only the difference that instead of the spikes 122 and 123 a I-like holding means 131 is provided, whose cross section is shown for instance in the case of the staple 101 in accordance with FIG. 10 in FIG. 10. The staple 101 is inserted into the U-like holding means 131, wherein it is retained by friction. The limbs 132 and 133 of the U-like holding means 131 are so short that on driving in the staples 101 they will just fail to reach the vertebra 18.

The instruments 120 and 130 for the staples preferably comprise an elongated instrument part 124 with an adjacent ramming part 128 and a set of insert parts with different spikes or, respectively, holding means for different staples.

Figure 14:
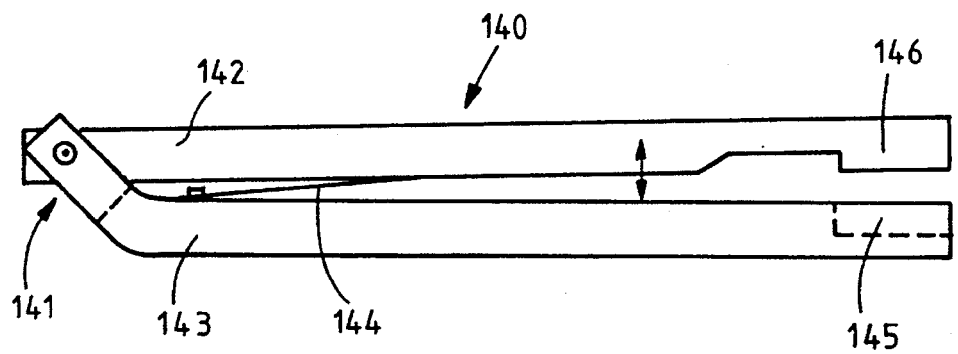
Figure 15:
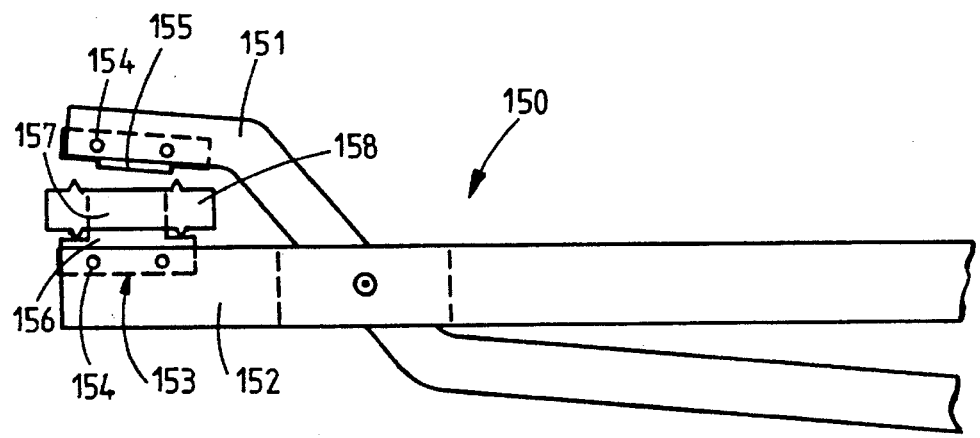

In FIGS. 14 and 15 the design of bone presses is illustrated. In accordance with FIG. 14 and press comprises two press halves 142 and 143 joined together and urged apart by a spring 144.

One half 143 of the press, constituting the lower half, has a recess 145 at the free end, into which the implant is placed. After filling of the implant cavity with bone substance the upper press half 142 is moved by hand against the action of the spring 144 toward the lower press half 143. A stamp 146 formed to correspond to the implant cavity on the free end of the upper press half 142 so compresses the bone substance that the substance is firmly seated in the implant. The bone press 140 illustrated in FIG. 14 is for example suitable for a U-like implant in accordance with FIG. 7a, the implant 70 being arranged with the transverse head projecting outward into the cavity 145. The upper press half only has a width equal to the clearance width of the intermediate space 79 in the implant 70.

The bone press 150 in accordance with FIG. 15 possesses two press halves 151 and 152 able to be moved like the jaws of a forceps, which are respectively provided with a recess 153 and two holes 153 in order to receive and hold press stamps 155 and 156 by means of pins. For different forms of implant only one bone press 150 and different press stamps 155 and 156 are required. In accordance with FIG. 15 two rectangular press stamps 155 and 156 are provided, which correspond to the cubic opening 157 in the implant 158.

Figure 16:
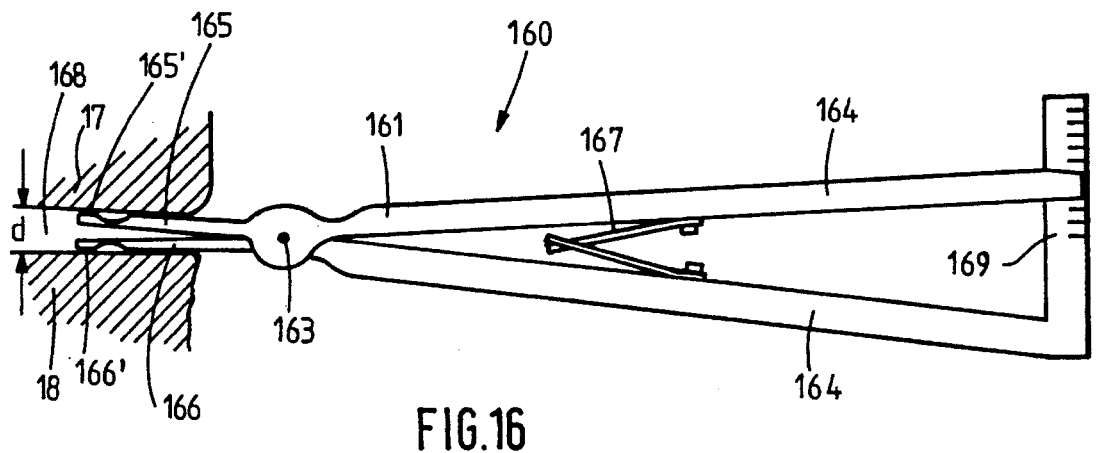
FIG. 16 shows a gap height measuring device.
Figure 17:
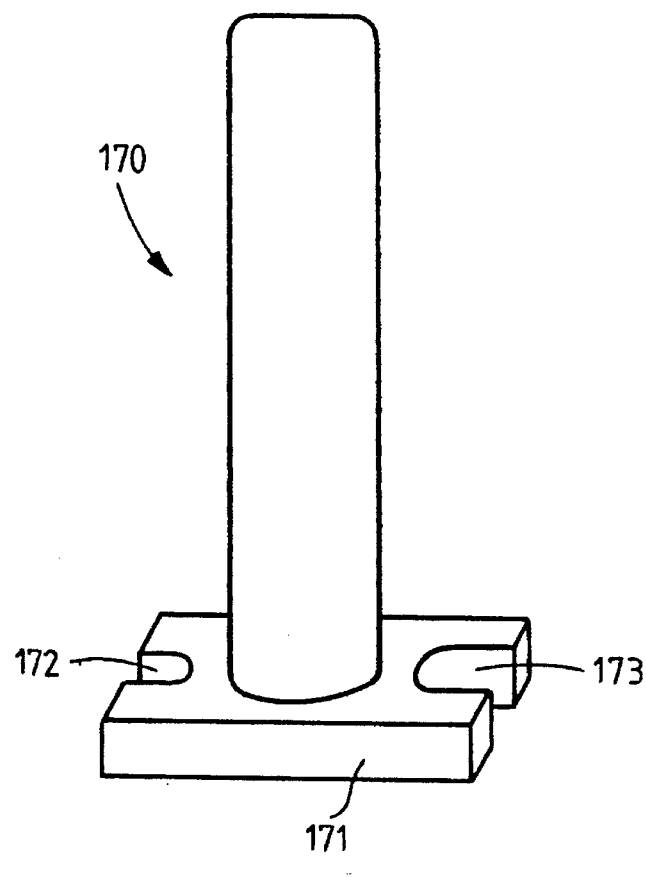
FIG. 17 shows a claw hammer.
Figure 18:
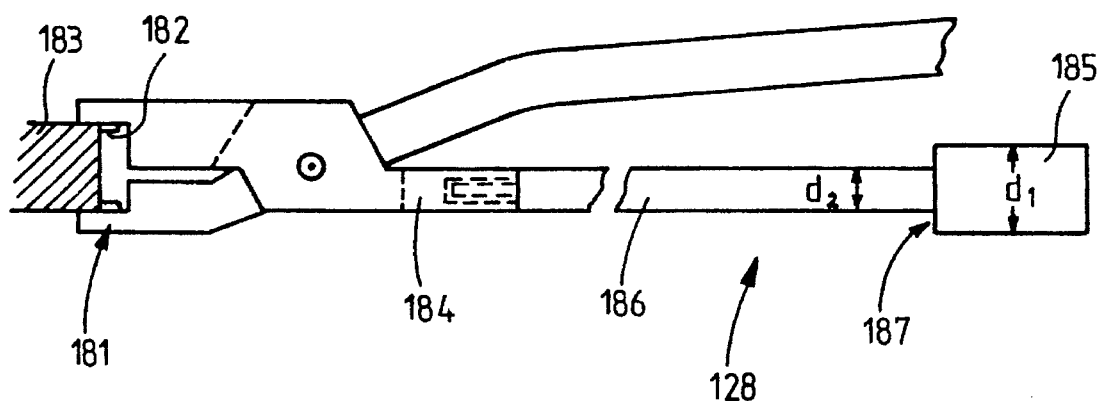
FIG. 18 shows a forceps for positioning in a rearward direction.

The instrument set can further comprise one intravertebral height measuring device or a temporary spreading device, for example in accordance with FIG. 16 and a reverse positioning instrument, as for example in accordance with FIGS. 17 and 18.

In FIG. 16 a spreading forceps 160 with a height measuring function is illustrated, which is constituted by two elongated elements 161 and 162 bent to be at an obtuse angle. At the bend part 163 the two elements are joined pivotally together in such a manner that on thrusting together the longer ends 164, against the action of a spring 167, the two shorter ends 165 and 166, which are introduced into the gap 168 between the vertebrae 17 and 18 and pressing against the vertebrae 17 and 18, are thrust apart. The vertebrae are thrust away from each other and the gap distance d is read off on a scale 169, which is connected with one of the two long ends. The position of measuring the height is defined by two measuring plates 165' and 166' provided at the tips of the two short ends 165 and 166. The spreading forceps may however be utilized also as a height measuring instrument only.

An implantation instrument set furthermore comprises a forceps for rearward positioning in order to extract an implant which has not been exactly placed or an implant inserted for testing. In FIG. 18 an example of this is depicted which is designed like a flat forceps. In the opening 181 of the forceps 180 spikes 182 are provided, which may bite into an implant 183 of synthetic resin, for example for more firmly anchoring the same.

The one handle 184 of the forceps is constituted by a screw-on ramming instrument 128. This ramming instrument 128 is also employed for other surgical implements, such as for example the instruments 120 and 130 for the insertion of staples. The ramming instrument 180 is therefore designed for being driven, i. e. knocked, in either direction since the instrument 128 has an impact head 185 at the free end whose diameter $d_1$ is larger than the diameter $d_2$ of the rod 186. Using a claw hammer 170 as depicted in FIG. 17 which fits around the rod 186, it is possible to direct blows onto the annular shoulder 187 in order to withdraw implants 183.

The claw hammer 170 in accordance with FIG. 17 has a hammer head 171 with two oppositely arranged slots 172 and 173 of different depth and different width. Such a claw hammer is suitable for ramming instruments 128 with a different rod diameter.

The spreading forceps 160 as shown in FIG. 16 is utilized in conjunction with a separate distance member for the preparation of the site of surgery. The distance member is so designed that after introduction of the spreading forceps 160 it is able to be placed in the gap 168 between the vertebrae 17 and 18. During the spreading operation the distance d is read off from the scale 169 and a distance member is selected from an assortment of such members and inserted.

FIGS. 19a and 19b show working embodiments of spacers. The spacer 190 in accordance with FIG. 10a essentially comprises two distance members 191 and 192, which are held at a distance from one another by means of a connecting element 193. The distance members 191 and 192 are held so far apart that they exert their supporting action at the edges 194 and 195 of the vertebrae so that the space required for the implantation operation between them remains free. After introduction of the spacer 190 the spreading forceps 160 is removed so that the opening is free for the surgeon.

Such a spacer may simultaneously be adapted to perform a guiding and/or positioning function. An extremely simple design is one in which, as shown in FIG. 19b, an open or split ring 193' on which two distance members 191' and 192' are fixedly mounted. The opening 196 of the ring 193 serves for the passage of the spreading forceps 160. On the ring 190' knobs or pins 197 are provided, which serve to couple up surgical implements. The surgical implement in accordance with FIG. 4 for example would have holes 49 instead of the spacing pins 48 so that the surgical implement 40 could be employed for the production of holes or for mounting implants on the suitably positioned pins 197 and is therefore able to be exactly positioned in relation to the vertebra 168. The distance members 191' and 192' as shown in FIG. 19b are U-like and their free ends are connected with the ring 193'.

The distance members 191 and 192 or, respectively, 191' and 192' arranged parallel to one another may also perform a guiding function.

The present invention is, of course, in no way restricted to the specific disclosure of the specification and drawings, but also encompasses any modifications within the scope of the appended claims.

I claim:

1. An implantation system for immobilizing vertebrae, said system comprising:

at least one guide instrument for mounting on vertebrae to be immobilized;

said guide instrument comprises at least two elongate, parallel guide rails assembled to form a unitary component, each of said guide rails having a longitudinal groove for guiding and exactly positioning surgical implants to be employed for surgery on the vertebrae, wherein said longitudinal grooves extend in a longitudinal direction of said guide instrument and face one another;

at least one elongate surgical implement guided with said guide instrument, said surgical implement having elongate first guide means for cooperating with said longitudinal grooves of said guide rails of said guide instrument; and surgical implants having means for immobilizing vertebrae, said surgical implants having second guide means for cooperating with said longitudinal grooves of said guide rails of said guide instrument.

2. An implantation system according to claim 1, wherein said guide instrument includes a spreading device having means for spreading vertebrae.

3. An implantation system according to claim 1, wherein said guide instrument further comprises inserts having means for adjusting a width between said longitudinal grooves of said guide instrument.

4. An implantation system according to claim 1, wherein said surgical implants are substantially U-shaped and have U-shaped end faces and wherein said second guide means are located on said U-shaped end faces of said surgical implants.

5. An implantation system according to claim 1, wherein said second guide means is at least one guide element in the form of a longitudinal key engaging said longitudinal keys of said guide rails of said guide instrument.

6. An implantation system according to claim 1, wherein each of said surgical implants is in the form of a rectangular block comprised of fiber reinforced synthetic resin.

7. An implantation system according to claim 1, further comprising said surgical implants having means for attaching said surgical implants to at least one vertebra, said means for attaching including staples.

8. An implantation system according to claim 1, wherein each of said surgical implants is in the form of a cylinder comprised of fiber reinforced synthetic resin.

9. An implantation system for immobilizing vertebrae, said system comprising:

at least one guide instrument for mounting on vertebrae to be immobilized; and said guide instrument comprises at least two elongate, parallel guide rails assembled to form a unitary component, each one of said guide rails having a longitudinal key for guiding and exactly positioning surgical implants to be employed for surgery on the vertebrae, wherein said longitudinal keys extend in a longitudinal direction of said guide instrument and face one another;

at least one elongate surgical implement guided with said guide instrument, said surgical implement having elongate first guide means for cooperating with said longitudinal keys of said guide rails of said guide instrument; and surgical implants having means for immobilizing vertebrae, said surgical implants having second guide means for cooperating with said longitudinal key of said guide rails of said guide instrument.

10. An implantation system according to claim 9, wherein said guide instrument includes a spreading device having means for spreading vertebrae.

11. An implantation system according to claim 9, wherein said guide instrument further comprises inserts having means for adjusting a width between said guide keys of said guide instrument.

12. An implantation system according to claim 9, wherein said surgical implants are substantially U-shaped and have U-shaped end faces and wherein said second guide means are located on said U-shaped end faces of said surgical implants.

13. An implantation system according to claim 9, wherein said second guide means is at least one guide element in the form of a longitudinal groove engaging said guide rails of said guide instrument.

14. An implantation system according to claim 9, wherein each of said surgical implants is in the form of a rectangular block comprised of fiber reinforced synthetic resin.

15. An implantation system according to claim 9, wherein each of said surgical implants is in the form of a cylinder comprised of fiber reinforced synthetic resin.

16. An implantation system according to claim 9, further comprising said surgical implants having means for attaching said surgical implants to at least one vertebra, said means for attaching including staples.

17. An implantation system for immobilizing vertebrae, said system comprising:

at least one guide instrument for mounting on vertebrae to be immobilized; and said guide instrument is in the form of an elongate, tubular component with internal elongate guide keys for guiding and exactly positioning surgical implants to be employed for surgery on the vertebrae, wherein said internal elongate guide keys extend in a longitudinal direction of said guide instrument and face one another;

at least one elongate surgical implement guided with said guide instrument, said surgical implement having elongate first guide means for cooperating with said internal elongate guide keys of said guide instrument; and surgical implants having means for immobilizing vertebrae, said surgical implants having second guide means for cooperating with said internal elongate guide keys of said guide instrument.

18. An implantation system according to claim 17, wherein said guide instrument includes a spreading device having means for spreading vertebrae.

19. An implantation system according to claim 17, wherein said guide instrument further comprises inserts having means for adjusting a width between said guide keys of said guide instrument.

20. An implantation system according to claim 17, wherein said surgical implants are substantially U-shaped and have U-shaped end faces and wherein said second guide means are located on said U-shaped end faces of said surgical implants.

21. An implantation system according to claim 17, wherein said second guide means is at least one guide element in the form of a longitudinal groove engaging said guide keys of said guide instrument.

22. An implantation system according to claim 17, wherein each of said surgical implants is in the form of a rectangular block comprised of fiber reinforced synthetic resin.

23. An implantation system according to claim 17, wherein each of said surgical implants is in the form of a cylinder comprised of fiber reinforced synthetic resin.

24. An implantation system according to claim 17, further comprising said surgical implants having means for attaching said surgical implants to at least one vertebra, said means for attaching including staples.

* * * * *